United States Patent
Martinez et al.

(10) Patent No.: US 8,592,587 B2
(45) Date of Patent: Nov. 26, 2013

(54) TRANSANNULAR REARRANGEMENT OF ACTIVATED LACTAMS

(75) Inventors: Jean Martinez, Caux (FR); Georges Dewynter, Montpellier (FR); Daniel Farran, Cabrieres (FR)

(73) Assignees: Centre National de la Recherche Scientifique (CNRS), Paris (FR); Universite de Montpellier I, Montpellier (FR)

( * ) Notice: Subject to any disclaimer, the term of this patent is extended or adjusted under 35 U.S.C. 154(b) by 129 days.

(21) Appl. No.: 12/532,067

(22) PCT Filed: Mar. 21, 2008

(86) PCT No.: PCT/EP2008/053449
§ 371 (c)(1),
(2), (4) Date: Sep. 18, 2009

(87) PCT Pub. No.: WO2008/125421
PCT Pub. Date: Oct. 23, 2008

(65) Prior Publication Data
US 2010/0099874 A1 Apr. 22, 2010

(30) Foreign Application Priority Data
Mar. 21, 2007 (FR) ...................... 0753973

(51) Int. Cl.
*C07D 215/00* (2006.01)
*C07D 487/02* (2006.01)
*C07D 209/38* (2006.01)
*C07D 295/00* (2006.01)

(52) U.S. Cl.
USPC ............. 546/16; 546/155; 548/453; 548/531; 548/513

(58) Field of Classification Search
USPC ...................... 546/16, 155; 548/453, 531, 513
See application file for complete search history.

(56) References Cited

U.S. PATENT DOCUMENTS 4,262,602 A 4/1981 Patil et al.
4,264,602 A 4/1981 Hardtmann

FOREIGN PATENT DOCUMENTS

DE 19 34 383 7/1969
FR 2 320 752 12/1976

OTHER PUBLICATIONS

Pothion et al. Tetrahedron Letters, 37(7), 1021030, 1996.*
Alcaraz et al. Tetrahedron, 53, 12443-12456.*
Oba et al. teach (Chemical Communication, 1196, 1875-1876.*
Dorwald F. A. Side Reactions in Organic Synthesis, 2005, Wiley: VCH, Weinheim p. IX of Preface p. 1-15.*
Farran et al.Journal of Peptide Science (2009), 15(7), 474-478.*
C. Alcaraz, A. Herrero, J-L. Marso, E. Fernandez-Alvarez, M. Bernabe; "Enantioselective Synthesis of (+)—(1R, 2S)—Allocoronanmic Acid," Tetrahedron Lett. 1992: 33, 5605-5608.
C. Alcaraz, D. Fernandez, M.P. De Frutos, J-L. Marso, M. Bernabe; "Asymmetric Syntheses of 1-Amino-2-Phenyl (Alkyl) cyclopropanecarboxylic Acids by Diastereoselective Cyclopropanation of Highly Functionalized Monochiral Olefines1#," Tetrahedron. 1994; 50, 12443-12456.
U. Schollkopf, U. Groth, D. Deng; "Enantioselective Synthesis of (R)-Amino Acids Using L-Valine as Chiral Agent," *Angew. Chem. Int. Ed. Engl.* 1981, 20, 798-799.
Oba, S. Nakajima, K. Nishiyama.; "Substituent-dependent asymmetric synthesis of L-threo-and L-erythro-[2, 3-$^2$H$_2$] phenylalanine from chiral (Z)-dehydrophenylalanine," *Chem. Comm.*, 1996, 1875-1876.
D. A. Peters, R.L. Beddoes, J.A. Joule; "Alternative Synthesis of 6-(3-Methoxybenzyl) pyrazin-2 (1*H*)-one. Synthesis of Indeno [1, 2-b] pyrazin-2-ones. Crystal Structures of 5-Acetoxy-1-benzyl-4-tert-butoxycarbonyl-6-(3-methoxybenzylidene)piperazin-2-one, 1-Benzyl-4-tert-butoxycarbonyl-7-methoxy-1,3,4,4a-tetrahydroindeno [1,2-b] pyrazin-2-one and 1-Benzyl-4-tert-butoxycarbonyl-7-methoxy-1,3,4,9-tetrahydroindeno-[1,2-b] pyrazin-2-one," *J. Chem. Soc. Perkin trans.I*; 1993, 1217-1224.
H.D. Dakin, R. West; A General Reaction of Amino Acids. II., J. *Biol. Chem.*; 1928, 78, 91, 745-756.
G. Hoefle, W. Steglich, H. Vorbrueggen; "4-Dialkylaminopyridines as Highly Active Acylation Catalysts," *Angew. Chem., Int. Ed. Engl.*, 1978, 17, 569-583.
U. Redeker, N. Engel, W. Steglich; "Uberfuhrung von n-acylaminosauren in enamine durch Beckmann-fragmentierung von α-acylaminoketoximen," *Tetrahedron Lett.*, 1981, XX, 4263-4264.
Dieckmann W., "Ueber ein ringformiges Analogon des Ketipinsaureesters," *Ber.*, 1894, 27, 102, 965; ibid 1900, 33, 595, 2670.
House H. O., Babad H.; "A New Synthesis of Cyclic Ketones," *J. Org. Chem.*, 1963, 28, 90-92.
Chakravarti R. N., Dutta N.; "Course of Cyclization in the Formation of Alicyclic Rings, Part III," *J. Ind. Chem. Soc.*, 1974, 51, 239-255.
Schaefer, John P., Bloomfield, Jordan J.; *Organic Reactions*, 1, 345; ibid, 15, 1.
S. Gabriel, J. Colman; "Ueber 4-Oxyisocarbostyril," *Berichte*, 1900, 33, 980, 996, 2630-2634. ibid. 1902, 35, 2421-2429.

(Continued)

*Primary Examiner* — Nizal Chandrakumar
(74) *Attorney, Agent, or Firm* — Harness, Dickey & Pierce, P.L.C.

(57) ABSTRACT

The disclosure relates to a method for the synthesis of a compound of the following formula (I) in which: R1 and R2 are independently an N-protective group; R3 is a hydrogen atom, a $C_1$-$C_6$ alkyl group, a $C_1$-$C_6$ arylalkyl group, a $C_2$-$C_6$ alkenyl group, or a alkoxycarbonylalkyl group; Y is a —C(HR4)- group in which R4 is a hydrogen atom, a $C_1$-$C_6$ alkyl group, an aryl group, a $C_1$-$C_6$ arylalkyl group, or a $C_2$-$C_6$ alkenyl group; or an orthophenylene group.

15 Claims, No Drawings

(56) References Cited

OTHER PUBLICATIONS

C.F.H. Allen; "The Naphthyridines," *Chem. Rev*, 1950, 47, 275-305.
J.H.M. Hill; "Mechanism of the Gabriel-Colman Rearrangement," *J. Org. Chem.* 1965, 30, 620-622.
L. Rugheimer, *Berichte*; "Ueber einen Abkommling des Tetrols and eine Synthese des Tribenzamidophloroglucins," 1888, 21, 3325-3331.
Oba, M.; Terauchi, T.; Owari, Y.; Imai, Y.; Motoyama, I.; Nishiyama, K.; "Stereo-divergent synthesis of L-threo- and L-erythro-[2,3-$^2$H$_2$] amino acids using optically active dioxopiperazine as a chiral template," *J. Chem. Soc., Perkin Trans.* 1 1998, 1275-1281.
J.J. Leban, K.L. Colson; "Base-Induced Dimerization of Urethane-Protected Amino Acid N-Carboxanhydrides," *J. Org. Chem.*; 1996, 61, 228-231.
C.J. Creighton, A.B. Reitz; "Synthesis of an Eight-Membered Cyclic Pseudo-Dipeptide Using Ring Closing Metathesis," *Org. Lett.* 2001, 3, 893-895.
A. Michaut, S. Miranda-Garcia, J.C. Menedez, J. Rodriguez; "Stereoselective Synthesis of Bicyclo [4.2.1] nonane Skeletons by Ring-Closing Metathesis: A New Versatile Methodology for the Efficient Assembly of Functionalized Cyclooctanoids," *Org. Lett.* 2004, 6, 3075-3078.
K. Wimalasena, M. P. D. Mahindaratne; "Chemistry of L-Ascorbic Acid: Regioselective and Stereocontrolled 2-C- and 3-C-Allylation via Thermal Claisen Rearrangement," *J. Org., Chem.*; 1994, 59, 3427-3432.
S.C. Gatling, J.E. Jackson; "Reactivity Control via Dihydrogen Bonding: Diastereoselection in Borohydride Reductions of α-Hydroxyketones," *J. Amer. Chem. Soc.*; 1999, 121, 8655-8656.
F.P.J.Y. Rutjes, H.E. Schoemaker; "Ruthenium-Catalyzed Ring Closing Olefin Metathesis of Non-Natural α-Amino Acids," *Tetrahedron Lett.* 1997, 38, 677-680.
R.H. Grubbs, S. Chang.; "Recent Advances in Olefin Metathesis and its Application in Organic Synthesis," *Tetrahedron*, 1998, 54, 4413-4450.
I. Ibnusaud, G. Thomas; "Biologically interesting chiral 3,4-disubstituted pyrrolidines from optically active hydroxycitric acid lactones," *Tetrahedron Lett.*, 2003, 44, 1247-1249.
K. Jadidi, R. Aryan, M. Mehrdad, T. Lugger, F. Ekkehardt Hahn, S. Weng Ng.; "Simple synthesis, structure and ab initio study of 1,4-benzodiazepine-2.5-diones," *J. Molec. Struct.* 2004, 692, 37-42.
B.B. Snider, M.V. Busuyek; "Synthesis of circumdatin F and sclerotigenin. Use of the 2-nitrobenzyl group for protection of a diketopiperazine amide; synthesis of ent-fumiquinazoline G," *Tetrahedron* 2001, 57, 3301-3307.
K. Fugi, T. Kawabata; "Memory of Chirality—A New Principle in Enolate Chemistry," *Chem. Eur. J.*; 1998, 3, 373-376.
P.R. Carlier, H. Zhao, J. DeGuzman, P.C.-H. Lam.; "Enantioselective Synthesis of 'Quaternary' 1,4-Benzodiazepin-2-one Scaffolds via Memory of Chirality," *J. Am. Chem. Soc.*; 2003, 125, 11482-11483.
H. Zhao, D.C. Hsu, P. Carlier; "Memory of Chirality: An Emerging Strategy for Asymmetric Synthesis," *Synthesis*, 2005, 1-16.
A. Klasek, K. Koristek, A. Lycka, M. Holcapek; "Reaction of 1-alkyl/aryl 1-3-amino-1H,3H-quinoline-2,4-diones with urea. Synthetic route to novel 3-(3-acylureido)-2,3-dihydro-1H-indo1-2-ones, 4-alkylidene-1'H-spiro[imidazolidine-5,3'-indole]-2,2'-diones, and 3,3a-dihydro-5H-imidazo[4,5-c]quinoline-2,4-diones," *Tetrahedron* 2003, 59, 5279-5288.
A. Klasek, A. Lycka, M. Holcapek, I. Hoza; "Reaction of 3-aminoquinoline-2,4-diones with nitrourea. Synthetic route to novel 3-ureidoquinoline-2,4-diones and imidazo[4,5-c]quinoline-2,4-diones," *Tetrahedron* 2004, 60, 9953-9961.
Kukla et al: "Synthesis and anti-HIV-1 activity of 4, 5, 6, 7-tetrahydro-methylimidazo [4, 5, 1-jk][ 1, 4] benzodiazepine-2 (1H)-one (TIBO) derivatives", *J. Med. Chem.* 1991, 34, 3187-3197.
Running, Jeffrey A., Peng, Susan, and Rosson, Reinhardt A., "The biotechnology of ascorbic acid manufacture," *Vit. C*, 2004, 49-64.
Reiter, Russel, J.; "Ascorbic acid in the central nervous system: uptake, distribution and functions," *Vit. C.*, 2004, 229-246.
Burger, R.M.; "Cleavage of Nucleic Acids by Bleomycin," *Chem. Rev.* 1998, 98, 1153-1169.
Boger, D.L.; Cai H.; "Bleomycin: Synthetic and Mechanistic Studies," *Angew, Chem. Int. Ed.* 1999, 38, 448-476.
Giordano, A; Della Monica, C, Landi F, Spinella A, Sodano G; "Stereochemistry and total synthesis of janolusimide, a tripeptide marine toxin," *Tetrahedrons Letters*, 2000, 41, 3979-3982.
Castejon, P; Moyano, A; Pericas M; Riera A; "Ready Access to Stereodefined β-Hydroxy-γ-amino Acids. Enantioselective Synthesis of Fully Protected Cyclohexylstatine," *Tetrahedrons*, 1996, 7063-7086.
Corey, EJ, Li W, Nagamitsu T; "An Efficient and Concise Enantioselective Total Synthesis of Lactacystin," *Angew. Chem. Int. Ed*, 1998, 37, 1676-1679.
Corey, EJ, Li W D; "Total Synthesis and Biological Activity of Lactacystin, Omuralide and Analogs," *Chem Parm. Bull*, 1999, 47, 1-10.
Burgstahler, A. W., Aiman C.E.; "A Direct Synthesis of DL-Baikiain," *J. Org. Chem*, 1960, 25, 489-492.
Archer, GA, Sternbaech, LH; "The Chemistry of Benzodiazepines," *Chem. Rev.* 1968, 68, 747.
Jones, GB, Davey, CL, Jenkins, TC, Kamal A, Kneile, GG, Neidle, S, Webster, GD, Thurston, DE; "The non-covalent interaction of pyrrolo[2, 1-c] [1, 4] benzodiazepine-5, 11-diones with DNA," *Anticancer Drug Des*. 5 1990, 249-264.
Kafka S, Klasek A, Polis J, Kosmrlj J, "Syntheses of 3-Aminoquinoline-2,4(1H,3H)-Diones," *Hetereocycles*, 2002, 57, 1659-1682.
Farran, D, Parrot, I, Martinez J, Dewynter, G; "Transannular Rearrangement of Activated Lactams: Stereoselective Synthesis of Substituted Pyrrolidine-2,4-diones from Diketopiperazines," *Angew, Chem. Int.* Ed. 2007, 46, 7488-7490.
Farran, D, Echalier, D, Martinez, J, Dewynter G; "Regioselective and sequential reactivity of activated 2,5-diketopiperazines," *J. Pept. Sci.* 2009; 15: 474-478.
Farran, D, Parrot, I, Toupet L, Martinez, J, Dewynter, G; "Transannular rearrangement of activated 2,5-diketopiperazines: a key route to original scaffolds," *Org. Biomol. Chem*, 2008, 6, 3989-3996.
Farran, D, Toupet L, Martinez, J, Dewynter, G; "Stereocontrolled Synthesis of 2,4-Diamino-3-hydroxyacids Starting from Diketopiperazines: A New Route for the Preparation of Statine Analogues," *Organic Letters*, vol. 9, n°23, 2007, 4833-4836.
Coursindel, T, Farran, D, Martinez, J, Dewynter, G; "[$^{15}$N]-Isotopic labeling: a suitable tool to study the reactivity of bis lactams," *Tetrahedrons letters*, 49 (2008), 906-909.
Branca, M, Pena, S, Guillot, R, Gori, D, Alezra, V, Kouklovsky, C; "Memory of Chirality of Tertiary Aromatic Amides: A Simple and Efficient Method for the Enantioselective Synthesis of Quaternary α-Amino Acids," *J. Am. Chem. Soc.* 2009, 131, 10711-10718.
Pothion et al: "Synthesis of pyrrolidine-2, 4-diones from urethane N-carboxyanhydrides (UNCAs)" Tetrahedron letters, Elsevier, Amsterdam, NL, vol. 37, n° 7, Feb. 12, 1996, pp. 1027-1030, XP004030219.
Podesva, C., et al.; "Synthesis and chemistry of 1-methyl-3-imino-4-hydroxy-4-phenyl-6-chloro-1,2,3,4-tetrahydroquinoline-2-one," Canadian Journal of Chemistry, 1968, 46, pp. 2263-2269.
Kobayashi, Shiro, et al; "Synthesis, Dimerization and Polymerization of 5-Oxazolones," Macromolecules 1986, 19, pp. 1547-1551.

\* cited by examiner

TRANSANNULAR REARRANGEMENT OF ACTIVATED LACTAMS

CROSS-REFERENCE TO RELATED APPLICATIONS

This application is a National Phase Entry of International Application No. PCT/EP2008/053449, filed on Mar. 21, 2008, which claims priority to French Patent Application No. 0753973, filed on Mar. 21, 2007, both of which are incorporated by reference herein.

BACKGROUND AND SUMMARY

The invention concerns a novel method allowing the simple, stereo-controlled synthesis of natural products, or of chiral intermediates for the synthesis of natural products. This method gives access to a series of molecules whose existing synthesis pathways are long and tedious.

Prior art methods for dimerization of urethane N-protected N-carboxyanhydrides (UNCAs) are always racemic and do not allow any structural diversity of the compounds obtained, since the R groups of the side chains are identical by definition. Unexpectedly, the rearrangement of the method according to the present invention is fully enantio-controlled, and the products obtained can be optically pure.

The method of the invention uses a rearrangement of activated lactams such as diketopiperazines and benzodiazepinediones under basic conditions. With the method of the invention it is possible to prepare aminotetramates and aminoquinoleines via a cycle reduction step concomitant with exclusion of an amino group, and optionally simultaneous substitution of the cycle. The invention also concerns a novel family of compounds of biological or pharmaceutical interest able to be obtained using the method of the invention.

More precisely the invention concerns a method to synthesize a compound of following formula (1):

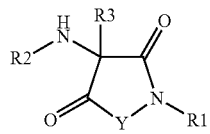
(I)

in which:

R1 and R2 are each independently an N-protecting group;

R3 is a hydrogen atom, a $C_1$ to $C_6$ alkyl group, a $C_1$ to $C_6$ arylalkyl group, a $C_2$ to $C_6$ alkenyl group or an alkoxycarbonylalkyl group;

Y is a —C(HR4)- group in which R4 is the hydrogen atom, a $C_1$ to $C_6$ alkyl group, an aryl group, a $C_1$ to $C_6$ arylalkyl group or a $C_2$ to $C_6$ alkenyl group; or an ortho-phenylene group, characterized in that it comprises:

a step ($a_1$) consisting of causing to react with a base the compound of following formula (II):

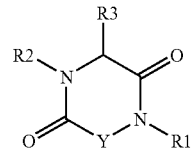
(II)

in which R1, R2, R3 and Y are as previously defined, or a step ($a_2$) consisting of causing to react with a base the compound of following formula (III):

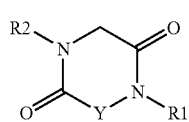
(III)

in the presence of a compound R3-X in which R1 and R2 are as defined previously, R3 is such as defined previously with the exclusion of hydrogen, and X is a halogen, or:

if Y is a —C(HR4)- group, a step ($a_3$) consisting of causing the compound of following formula (IV) to react with a base:

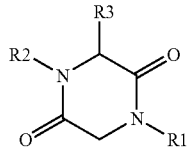
(IV)

in the presence of a compound of formula R4-X in which R1, R2, R3 are as previously defined, R4 is as previously defined with the exclusion of hydrogen, and X is a halogen, or:

if Y is a —C(HR4)- group, a step ($a_4$) consisting of causing to react with a base the compound of following formula (V):

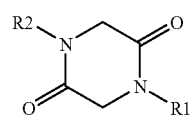
(V)

in the presence of a compound of formula R4-X, in which R1 and R2 are as previously defined, R3 is identical to R4 and is as defined previously with the exclusion of hydrogen, and X is a halogen.

X is advantageously Cl or Br.

By the term "$C_1$ to $C_6$ alkyl group" in the meaning of the present invention is meant any alkyl group with 1 to 6 carbon atoms, straight or branched, in particular the methyl, ethyl, n-propyl, isopropyl, n-butyl, iso-butyl, sec-butyl, t-butyl, n-pentyl, n-hexyl groups. Advantageously, it is a methyl or isopropyl group. By the term "$C_2$ to $C_6$ alkenyl group" in the meaning of the present invention is meant any alkenyl group with 2 to 6 carbon atoms, straight or branched, in particular the vinyl or allyl group, advantageously an allyl. By the term "aryl group" in the meaning of the present invention is meant one or more aromatic cycles having 5 to 8 carbon atoms able to be joined or fused. In particular, the aryl groups may be monocyclic or bicyclic groups, preferably phenyl, naphthyl, tetrahydronaphthyl or indanyl. Advantageously it is a phenyl group.

By the term "$C_1$ to $C_6$ arylalkyl group" in the meaning of the present invention is meant any aryl group such as defined above, linked via a $C_1$ to $C_6$ alkyl group such as defined above. In particular an arylalkyl group is a benzyl group. By the term "alcoxy group" in the meaning of the present invention is meant any alcoxy group with 1 to 6 carbon atoms, straight or branched, in particular the $OCH_3$ and $OC_2H_5$ groups. By the term "alcoxycarbonyl group" in the meaning of the present invention is meant any alcoxy group as previously defined linked via a carbonyl group. One example of an alcoxycarbonyl group is the acetyl group. Advantageously it is a tert-butyloxycarbonyl group.

By the term "aryloxy group" in the meaning of the present invention is meant any aryl group such as defined above, linked via an oxygen atom. Advantageously it is the benzyloxy group. By the term "aryloxycarbonyl group" in the meaning of the present invention is meant any aryloxy group such as defined above, linked via a carbonyl group. Advantageously the aryloxycarbonyl group is the carbobenzyloxy group. By the term "alkoxycarbonylalkyl group" in the meaning of the present invention is meant any alcoxy group such as defined above, linked via a carbonyl itself linked via an alkyl group such as defined above. Advantageously, it is a $CH_2COOC_2H_5$ or $CH_2CH_2COOCH_3$ group.

By the term "N-protecting group" in the meaning of the present invention is meant any substituent which protects the $NH_2$ group against adverse reactions such as the N-protecting groups described in Greene: "Protective groups in Organic Synthesis" (John Wiley & Sons, New York [1981]) and Harrison et al "Compendium of Synthetic Organic Methods", Vols. 1 to 8 (J. Wiley & Sons, 1971 to 1996). The N-protecting groups comprise carbamates, amides, N-alkyl derivatives, amino acetal derivatives, N-benzyl derivatives, imine derivatives, enamine derivatives and N-heteroatom derivatives. In particular, the N-protecting group comprises formyl, acetyl, benzoyl, pivaloyl, phenylsulfonyl, benzyl (Bn), t-butyloxycarbonyl (boc), benzyloxycarbonyl (cbz), p-methoxybenzyloxycarbonyl, p-nitrobenzyloxycarbonyl, trichloroethoxycarbonyl (troc), allyloxycarbonyl (alloc), 9-fluorenylmethyloxycarbonyl (Fmoc), trifluoro-acetyl, benzyl carbamates (whether or not substituted) and similar. It is advantageous to use either boc or cbz as N-protecting group on account of their relatively easy removal, for example using moderate acids for boc e.g. trifluoroacetic acid or hydrochloric acid in ethyl acetate; or by catalytic hydrogenation for cbz. Advantageously it is the boc group. By the term "halogen atom" in the meaning of the present invention is meant any halogen atom, advantageously chosen from among Cl, Br, I or F.

Under the present invention, by "pharmaceutically acceptable" is meant which can be used for the preparation of a pharmaceutical composition which is generally safe, non-toxic and not undesirable either biologically or otherwise, and which is acceptable for veterinary use and for human pharmaceutical use. By "pharmaceutically acceptable salts" is meant a compound of salts which are pharmaceutically acceptable as defined herein, and which have the desired pharmacological activity of the parent compound. Said salts comprise:

(1) acid addition salts formed with inorganic acids such as hydrochloric acid, hydrobromic acid, sulphuric acid, nitric acid, phosphoric acid and similar; or formed with organic acids such as acetic acid, benzene sulphonic acid, benzoic acid, camphor sulphonic acid, citric acid, ethane-sulphonic acid, fumaric acid, glucoheptonic acid, gluconic acid, glutamic acid, glycolic acid, hydroxynaphtoic acid, 2-hydroxyethanesulphonic acid, lactic acid, maleic acid, malic acid, mandelic acid, methanesulphonic acid, muconic acid, 2-naphtalenesulphonic acid, propionic acid, salicylic acid, succinic acid, dibenzoyl-L-tartaric acid, tartaric acid, p-toluenesulphonic acid, trimethylacetic acid, trifluoroacetic acid and similar; or (2) the salts formed when an acid proton present in the parent compound is either replaced by a metallic ion e.g. an alkaline metal ion, an alkaline-earth metal ion or an aluminium ion; or coordinates with an organic or inorganic base. Acceptable organic bases comprise diethanolamine, ethanolamine, N-methylglucamine, triethanolamine, tromethamine and similar. Acceptable inorganic bases comprise aluminium hydroxide, calcium hydroxide, potassium hydroxide, sodium carbonate and sodium hydroxide.

The preferred pharmaceutically acceptable salts are salts formed from hydrochloric acid or trifluoroacetic acid.

The compounds of the invention all have a centre of asymmetry and can therefore exist in the form of optical isomers. The present invention comprises these isomers both separately and as a mixture. However, advantageously the method according to the present invention is fully enantio-controlled and the compounds obtained are optically pure.

Advantageously, if Y is the ortho-phenylene group, step ($a_1$) consists of causing to react with a base the compound of following formula (VI):

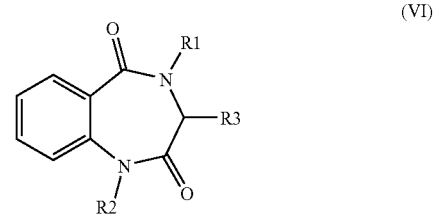

in which R1, R2 and R3 are as previously defined.

R1 and R2 may advantageously be chosen independently of each other from the group comprising $C_1$ to $C_6$ alcoxycarbonyls, aryloxycarbonyls and benzoyl, preferably tert-butyloxycarbonyl or carbobenzyloxy. R1 and R2 are advantageously tert-butyloxycarbonyl. R3 and R4 may advantageously each be chosen independently from the group comprising isopropyl, benzyl, methyl, sec-butyl, prenyl (or 3,3-dimethylallyl), allyl, —$CH_2COOC_2H_5$ and —$CH_2CH2COOCH_3$.

The base can be chosen from the group comprising potassium tert-butylate, sodium hydride, lithium diisopropylamine, lithium hexamethyldisilazane, potassium hexamethyldisilazane and dimethylaminopyridine. The base is advantageously potassium tert-butylat or lithium hexamethyldisilazane or sodium hydride. Advantageously for step ($a_1$) the base is potassium tert-butylate. In this case step ($a_1$), after the reaction with the base, may comprise a washing step with HCl. Advantageously for steps (a2), (a3) or (a4) the base is lithium hexamethyldisilazane or sodium hydride. The reaction solvent is an organic solvent, advantageously tetrahydrofurane (THF).

Advantageously, the reaction takes place at room temperature. However, it may also take place at a lower temperature, advantageously at a temperature of between −78° C. and room temperature, advantageously at 0° C. or at −78° C. In particular, the reaction temperature depends on the base used. With NaH therefore the temperature is advantageously 0° C., with LIHMDS the temperature is advantageously −78° C., and with tBuOK the reaction advantageously takes place at room temperature.

If Y is a —C(HR4)- group and R3 and R4 are identical and represent an allyl group, the method comprises an additional step ($b_1$) consisting of submitting the compound of formula (I) to an intramolecular metathesis reaction of the olefins to give the compound of following formula (VII):

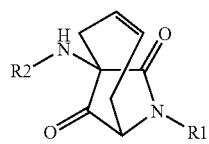
(VII)

in which R1 and R2 are such as previously defined.

If Y is the —C(HR4)- group, the method comprises the following additional successive steps consisting of:

($b_2$) causing the compound of formula (I) to react in a basic medium with an allyl halide to give the following compound (VIII):

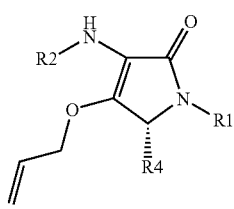
(VIII)

in which R1, R2 and R4 are such as defined previously, preferably R4 is isopropyl, (c) converting by heating, preferably in a microwave, the compound of formula (VIII) into following compound of formula (IX):

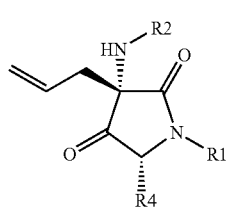
(IX)

in which R1, R2 and R4 are such as defined previously, preferably R4 is isopropyl, (d) causing the compound of formula (IX) to react with an allyl halide to form the following compound of formula (X):

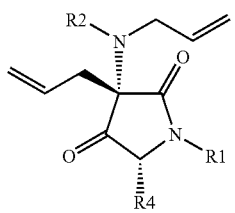
(X)

in which R1, R2 and R4 are such as previously defined, preferably R4 is isopropyl, and (e) converting the compound of formula (X) by intramolecular metathesis of the olefins, into following compound of formula (XI):

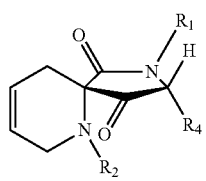
(XI)

in which R1, R2 and R4 are such as defined previously, preferably R4 is isopropyl. Advantageously, this metathesis cyclization is performed according to Grubbs. Advantageously steps (c) and (d) are a Claisen-type rearrangement.

If R3 is the EtOOCCH$_2$ group and Y is the —C(HR4)- group, the method comprises an additional step ($b_3$) consisting of causing the compound of formula (I) to react with a hydride, advantageously a borohydride, advantageously NaBH4 to form the following compound of formula (XII):

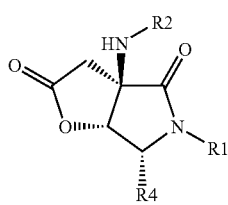
(XII)

in which R1, R2 and R4 are as defined previously, preferably R4 is isopropyl.

If Y is a —(CHR4)- group, the method comprises an additional step ($b_4$) consisting of causing the compound of formula (I) to react with trifluoroacetic acid, advantageously at a weight concentration of between 3% and 10%, preferably 5%, to give the following compound of formula (XIII):

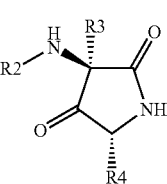
(XIII)

in which R2, R3 and R4 are such as previously defined, preferably R4 is isopropyl.

If Y is a —(CHR4)- group, the method comprises an additional step (c4) consisting of causing the compound of formula (XIII) to react with a hydride, preferably a borohydride and more preferably NaBH4 to form the following compound of formula (XIV):

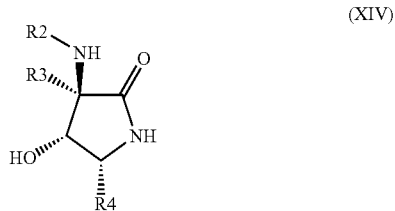

in which R2, R3 and R4 are such as previously defined, preferably R4 is isopropyl.

If Y is a —(CHR4)- group, the method comprises an additional step (c5) consisting of causing the compound of formula (XIII) to react with trifluoroacetic acid, advantageously at a weight concentration of between 10% and 25%, preferably 15%, to give the following compound of formula (XV):

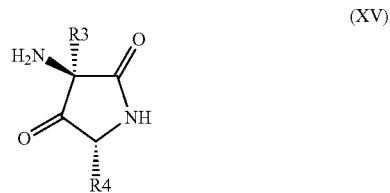

in which R3 and R4 are such as defined previously, preferably R4 is isopropyl.

If Y is the —(CHR4)- group, the method comprises an additional step (b5) consisting of causing the compound of formula (I) to react with a borohydride, preferably NaBH4, to form the following compound of formula (XVI):

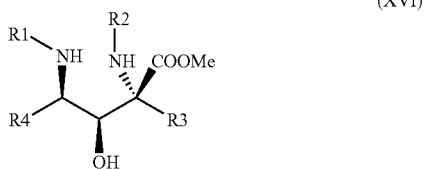

in which R1, R2, R3 and R4 are such as defined previously.

A further subject of the invention is the following compound (XVII):

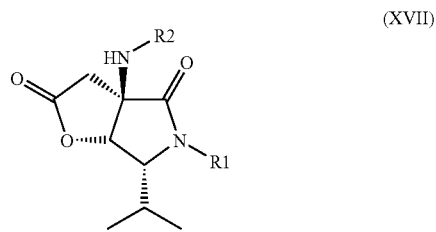

and its pharmaceutically acceptable salts, in which R1 and R2 are each independently an N-protecting group, and the compounds of following formula (XVIII):

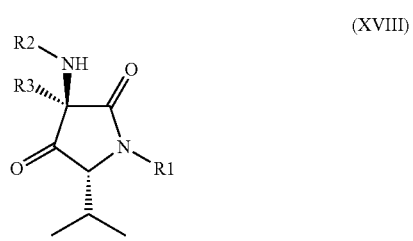

and its pharmaceutically acceptable salts, in which:

R1 and R2 are each independently an N-protecting group

R3 is a methyl, benzyl, isopropyl, allyl, prenyl group or —CH$_2$COOC$_2$H$_5$.

Advantageously regarding the compounds of formula (XVIII), the following compound:

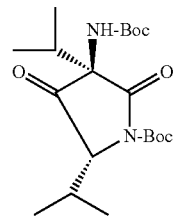

is excluded.

The methods of the present invention open up an additional pathway to several families of molecules of major biological or pharmaceutical interest, which have been the subject of numerous research studies or publications. These methods effectively give access to a variety of key intermediates in the total synthesis of biologically active molecules, or allow compounds to be synthesized which have properties of interest.

Therefore the compounds of formula (VIII) are structurally comparable to vitamin C, well known inter alia for its antioxidant properties. The compounds of formula (XVI) have the peptide sub-structure of bleomycin (antibiotic and anticancer agent), of janolusimide and statins (enzyme inhibitors). The compounds of formula (XII) are similar to mescaline isocitrimide lactone, a psycho-active substance derived from mescal. The compounds of formula (VI) are related to compounds having anti-tumour, anti-HIV, anti-hypertensive, anti-inflammatory, analgesic properties, and have a relaxing effect on muscles.

DETAILED DESCRIPTION

The invention will now be illustrated in non-limiting manner by the following examples.

Example 1

Synthesis of 1-tert-butoxycarbonyl-4-hydroxy-3-tert-butyloxycarbonylamino-1,5-dihydropyrrol-2-one (I-a)

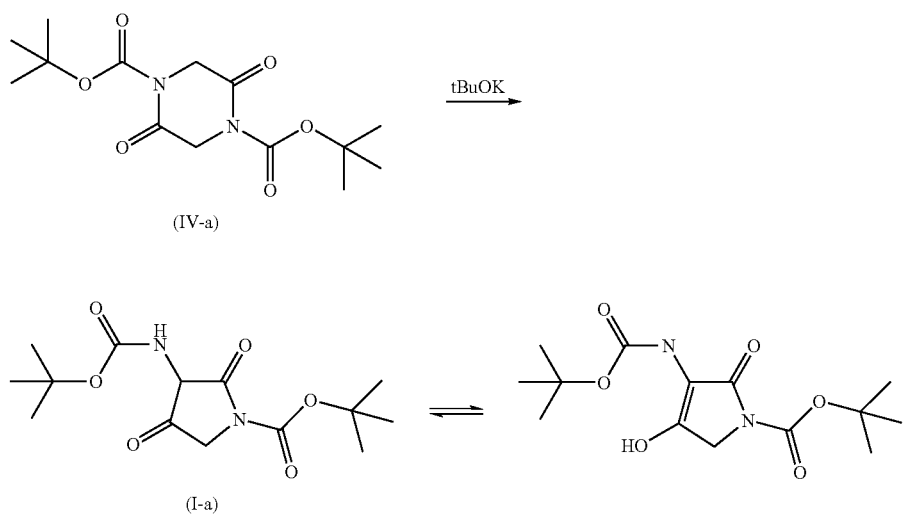

At room temperature t-BuOK (0.312 g, 2.78 mmol) was added to a solution of substituted piperazine-2,5-dione (IV-a) (0.794 g, 2.53 mmol) in dehydrated THF (10.3 mL). The solution was stirred 12 hours under an argon atmosphere. The medium was then diluted with AcOEt (20 mL), washed with a 0.1N HCl solution, and dried over anhydrous $MgSO_4$. The solvent was removed in vacuo and the crude residue purified by chromatography on a silica gel column (dichloromethane/MeOH 100:0→90:10). The lactam (I-a) is isolated in the form of a colourless solid (0.575 g) corresponding to the enolic form.

Yield=72% (pure compound). Melting point=65° C., not corrected.

$^1$H-NMR ($CDCl_3$, 200 MHz): δ 1.51 (s, 9H, $CH_3C$); 1.55 (s, 9H, $CH_3C$); 4.16 (s, 2H, $CH_2$); 6.65 (sl, 1H, NH); (DMSO-d6, 200 MHz): δ 1.40 (s, 9H, $CH_3C$); 1.46 (s, 9H, $CH_3C$); 4.12 (s, 2H, $CH_2$); 7.84 (sl, 1H, NH); 11.96 (m, 1H, OH).

$^{13}$C-NMR ($CDCl_3$, 100 MHz): δ 28.0 ($CH_3C$); 47.0 ($CH_2$); 83.1 and 83.3 ($CCH_3$); 104.1 (CvinN); 148.9 and 155.7 (CO carbamate); 150.8 (CvinO); 165.1 (CO lactam). LC/MS: tr=3.84 min; 646, [2M+NH4$^+$]; 629; [[2M+H$^+$]; 332, [M+NH4$^+$]; 315, [M+H$^+$], 259, [(M+H$^+$)-tBu]; 203, [(M+H$^+$)-2tBu]; 159 (M+H$^+$)-2boc]. tr=2.66 min 2 with loss of a Boc group in situ: 215 [(M+H$^+$-Boc)]. HPLC=11.46 min.

Example 2

Synthesis of (3S,5S) 1-tert-butoxycarbonyl-3-tert-butoxycarbonylamino-3,5-dimethylpyrrolidine-2,4-dione (I-b1) and (3R,5S) (I-b2)

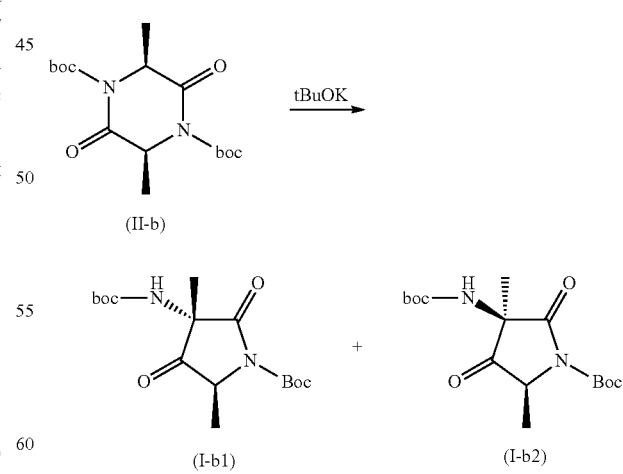

The compounds were synthesized following the above-described procedure.

(I-b1) (3S,5S); melting point=104° C. (not corrected); (α) D20=−9.0 (c=2.12, dichloromethane). $^1$H-NMR ($CDCl_3$, 200 MHZ): δ 1.35 (s, 9H, CH$_3$C); 1.40 (d, 3H, CH$_3$); 1.52 (s, 3H, CH$_3$quat); 1.54 (s, 9H, CH$_3$C); 4.52 (q, 1H, CH*, J=7.1 Hz); 5.54 (sb, 1H, NH), nOe between CHαAla and NH Boc. $^{13}$C-NMR (CDCl$_3$, 100 MHz): δ 17.9, 20.2 (CH$_3$ Ala); 28.0, 28.1 (CH$_3$C Boc); 59.5 (Cquat); 60.6 (CH*); 81.5, 84.0 (CCH$_3$); 149.0, 154.9 (CO carbamate); 172.0 (CO lactam); 207.1 (CO ketone). LC/MS: tr=3.75 min; 343 [M+H$^+$]; 287 [(M+H$^+$)-tBu]; 231 [(M+H$^+$)-2tBu]. HR-MS 343.1870 Th (calculated=343.1869 Th). HPLC; tr=11.153 min.

(I-b1) (3R,5S); melting point=159° C. (not corrected); [α]D20=−101.3 (c=1.57, dichloromethane). $^1$H-NMR (CDCl$_3$, 200 MHz): δ 1.41 (s, 9H, CH$_3$C); 1.43 (s, 3H, CH$_3$Cquat); 1.59 (s, 9H, CH$_3$C); 1.69 (d, 3H, CH$_3$CH*, J=6.6 Hz); 4.47 (q, 1H, CH*, J=6.7 Hz); 5.23 (sb, 1H, NH), NOe between CHα Ala and CH$_3$Cquat, and between CH$_3$CH* and NH-Boc. $^{13}$C-NMR (CDCl$_3$, 100 MHz): δ 16.4 (CH3CH*); 19.8 (CH$_3$Cquat); 28.0, 28.1 (CH$_3$C); 59.9 (CH*); 60.0 (Cquat), 81.4, 84.0 (CCH$_3$); 149.1, 154.4 (CO carbamate); 171.6 (CO lactam); 207.2 (CO ketone). LC/MS: tr=3.90 min: 343 [M+H$^+$]; 287 [(M+H$^+$)-tBu]; 231 [(M+H$^+$)-2tBu]; 143 [(M+H$^+$)-2boc]. HR-MS 343.1870 Th (calculated=34.1869 Th). HPLC tr=11.602 min.

Example 3

Synthesis of 1-tert-butoxycarbonyl-3-benzyl-3-tert-butoxycarbonylaminopyrrolidine-2,4-dione (I-c), 1-tert-butyloxycarbonyl-3-tert-butoxycarbonylamino-3,5-dibenzylpyrrolidine-2,4-dione (I-d), and 3-tert-butyloxycarbonylamino-3,5-diallyl-1-tert-butoxycarbonylpyrrolidine-2,4-dione (I-e)

concentrated in vacuo. The crude mixture of alkylated compounds was purified by chromatography on silica gel column (dichloromethane-AcOEt) which successively gave the compounds (I-d) (0.092 g) and (I-c) (0.058 g) in the form of colourless powders.

(I-c): melting point 126° C. (not corrected). $^1$H-NMR (DMSO-d6, 200 MHz): δ 1.36 (s, 9H, CH$_3$C); 1.40 (s, 9H, CH$_3$C); 2.93, 3.90 (dd, 2H, CH$_2$, Gly, JAB=18.4 Hz); 2.96, 3.05 (dd, 2H, CH$_2$Ph, JAB=12.6 Hz); 7.00-7.35 (m, 5H, Harom); 8.42 (s, 1H, NH), nOe detected between the most protected proton of Gly methylene (proS) and the aromatic protons. $^{13}$C-NMR (CDCl$_3$, 100 MHz): δ 27.9, 28.2 (CH$_3$C); 40.5 (CH$_2$Ph); 54.6 (CH$_2$ Gly); 65.2 (CCH$_2$Ph); 81.9, 83.7 (CCH$_3$); 126.6-135.7 (Carom); 148.3, 154.8 (CO carbamates); 171.0 (CO lactam). HPLC: tr=12.779 min. LC/MS: tr=4.40 min, 809 [2M-+H$^+$]; 405 [M+H$^+$]; 349 [(M+H$^+$)-tBu]; 305 [(M+H$^+$)-Boc]; 249 [(M+H$^+$)-Boc-tBu]; 205 [(M+H$^+$)-2Boc]. HR-MS: 405.2048 Th (calculated=405.2026 Th); C21H28N2O6.

(I-d): melting point 147° C. (not corrected). $^1$H-NMR (DMSO-d6, 200 MHz): δ 1.32 (s, 9H, CH$_3$C); 1.45 (s, 9H, CH$_3$C); 1.65, 2.30 (ddd, 2H, CH*CH$_2$Ph, JAB=13.9 Hz, JAX=8.8 Hz, JBX=4.3 Hz); 2.62, 2.97 (dd, 2H, Cquat CH$_2$Ph, JA'B'=13.3 Hz); 4.3, 4.44 (dd, 1H, JAX=8.7 Hz, JBX=4.3 Hz); 6.98-7.44 (m, 5H, Harom); 8.31 (s, 1H, NH). $^{13}$C-NMR (CDCl$_3$, 100 MHz): δ 28.1 (CH$_3$C); 34.9 (CH*CH$_2$Ph); 37.7 (CquatCH$_2$Ph); 61.8 (CquatCH$_2$Ph); 66.1 (CH*CH$_2$Ph); 81.6, 84.3 (CCH$_3$); 128.3, 130.8 (Carom); 149.3, 154.9 (CO carbamate); 171.4 (CO lactam); 205.4 (CO ketone). HPLC tr=14.50 min.

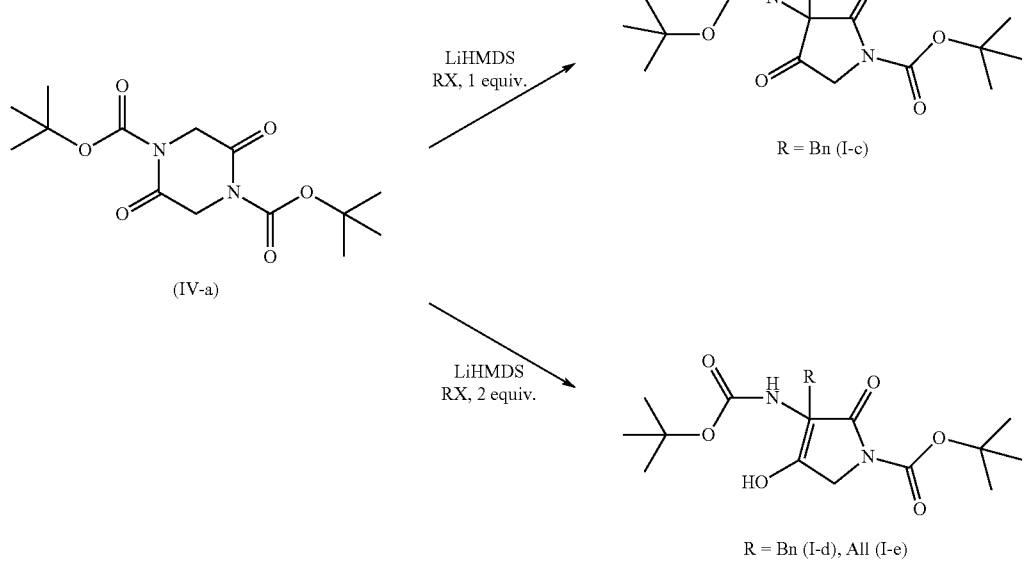

To a stirred solution of compound (IV-a) (0.237 g, 0.75 mmol) in dehydrated THF (3.8 ml), was added dropwise a solution of 1.06 M LiHMDS in THF (1.78 mL, 1.89 mmol) at −78° C. under an argon atmosphere. After 45 min, benzyl bromide was added (0.20 mL, 1.66 mmol). The reaction mixture was left at room temperature for 12 hours then diluted with AcOEt (10 mL) and washed with a 0.1N HCl solution. The organic phase was dried over MgSO$_4$ and the solvent was LC/MS: tr=4.99 min: 495 [M+H$^+$]; 439 [(M+H$^+$)-tBu]; 395 [(M+H$^+$)-Boc]; 339 [(M+H$^+$)-Boc-tBu]; 295 [(M+H$^+$)-2Boc]. HR-MS: 495.2528 Th (calculated=495.2495 Th) C28H34N2O6.

(I-e): prepared by analogy with allyl bromide. Colourless oil (mixture of geometric isomers).

$^1$H-NMR (CDCl$_3$, 200 MHz); δ 1.37 (s, 9H, CH$_3$C); 1.39 (s, 9H, CH$_3$C); 1.58 (s, 9H, CH$_3$C); 1.64 (s, 9H, CH$_3$C);

2.31-2.61 (m, 4H, CquatCH$_2$CH=CH$_2$); 2.61-3.05 (m, 4H, CH* CH$_2$CH=CH$_2$); 4.22-4.31 (m, 1H, CH*); 4.56-4.66 (m, 1H, CH*); 5.04-5.35 (m, 10H, NH and CH$_2$=CH); 5.53-6.14 (m, 4H, CH=CH$_2$).

LC/MS tr=4.38 min: 395 [M+H$^+$]; 339 [(M+H$^+$)-tBu]; 295 [(M+H$^+$)-Boc]; 283 [(M+H$^+$)-2 tBu].

Example 4

Synthesis of the tert-butyl ester of 7-tert-butoxycarbonyl-8,9-dioxo-7-aza-bicyclo[4.2.1.]non-3-in-1-yl carbamic acid (VII-e)

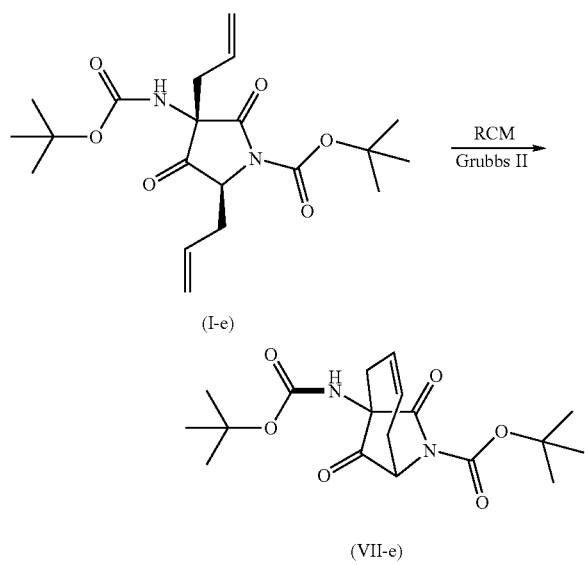

To a refluxed solution of bis-allyltetramate (I-e) (0.226 g, 0.57 mmol) in freshly distilled dichloromethane (8 mL) the addition was made of benzylidene-[1.3-bis-(2,4,6-trimethylphenyl-2-imidazolidinylidene]-dichloro (tricyclohexylphosphane) ruthenium (Grubbs II reagent) (0.010 g, 0.0115 mmol). The solution was stirred for 30 min at 45° C. and deactivated with DMSO (0.04 mL, 0.58 mmol, 50 equiv relative to the catalyst). After stirring 12 hours at ambient temperature the solvent was concentrated in vacuo and the crude residue purified by chromatography on silica gel column (dichloromethane/AcOEt (100:0→85:15). The bicyclical compound (VII-e) was collected in the form of a white solid (0.144 g). Yield 70%. Melting point: 104° C. (not corrected).

$^1$H-NMR (CDCl$_3$, 200 MHz): δ 1.35 (s, 6H, CH$_3$C); 1.42 (s, 3H, CH$_3$C); 1.54 (s, 9H, CH$_3$C); 2.22-2.33 and 2.55-2.68 (m, 2H, CH$_2$Cquat); 2.36-2.48 and 2.80-2.92 (m, 2H, CH$_2$CH*); 4.58 (m, 0.3H, CH*); 4.70 (m, 0.7H, CH*); 5.40 (s, 1H, NH); 5.46 to 5.61 (m, 2H, CH=CH). E/Z isomerism on the Boc-lactam group was probably responsible for duplication of the tBu-related signal and the signal of the neighbouring CH*. $^{13}$C-NMR (CDCl$_3$, 100 MHz): δ 28.0 and 28.2 (CH$_3$C); 30.3, 33.7 (CH$_2$); 62.0 (CH*); 64.4 (Cquat); 81.6, 84.2 (CCH$_3$); 121.19, 124.5 (CH=CH); 148.4, 154.6 (CO carbamate); 170.3 (CO lactam); 204.7 (CO ketone). HPLC tr=10.937 min. LC/MS: tr=3.89 min: 367 [M+H$^+$]; 311 [(M+H$^+$)-tBu] 267 [(M+H$^+$) Boc]. C18H26N2O6.

Example 5

Synthesis of (3R,5R) 1-tert-butoxycarbonyl-3-tert-butoxycarbonylamino-5-isopropyl-3-methylpyrrolidine-2,4-dione (I-f), (3R,5R) 1-tert-butoxycarbonyl-3-tert-butoxycarbonylamino-5-isopropyl-3-benzylpyrrolidine-2,4-dione (I-g) and (3R,5R) 1-tert-butoxycarbonyl-3-tert-butoxycarbonylamino-5-isopropyl-3-allylpyrrolidine-2,4-dione (I-h)

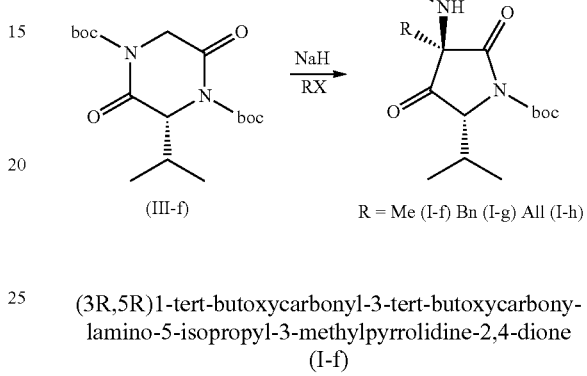

(3R,5R)1-tert-butoxycarbonyl-3-tert-butoxycarbonylamino-5-isopropyl-3-methylpyrrolidine-2,4-dione (I-f)

A suspension of 60% NaH in mineral oil (0.076 g, 3.17 mmol) was diluted in dehydrated THF (60 mL). A solution of piperazinedione 3 (0.753 g, 2.11 mmol) dissolved in dehydrated THF was added dropwise at 0° C. under an argon atmosphere. The reaction was stirred 1 hour and methyl iodide (0.16 mL, 2.54 mmol) was added. After 12 hours' stirring, AcOEt (24 mL) was added. The organic phase was washed with 0.1N HCl, dried over MgSO$_4$ and concentrated in vacuo. The crude residue was then purified by chromatography on silica gel column (petroleum ether/AcOEt 100:0→50:50). The compound (I-f) was obtained in the form of a white powder (0.450 g, yield 60%).

Melting point: 111° C. (not corrected). [α]D20=+1 1 (c=2.10 dichloromethane)

$^1$H-NMR (CDCl$_3$, 200 MHz): δ 0.93 (d, 3H, CH$_3$CH, J=7.0 Hz); 1.20 (d, 3H CH$_3$CH, J=7.1 Hz); 1.36 (s, 9H, CH$_3$C); 1.38 (s, 3H, CH$_3$Cquat); 1.56 (s, 9H CH$_3$C); 2.32-2.50 (m, 1H, CH CH$_3$); 4.53 (d, 1H, CH*, J=4.2 Hz); 5.36 (sb, 1H, NH). $^{13}$C-NMR (CDCl$_3$, 100 MHz): δ 16.5, 17.8 (CH$_3$CH); 18.7 (CH$_3$Cquat); 28.0 (CH$_3$C); 29.7 (CH); 59.3 (Cquat); 69.9 (CH*); 81.3, 83.8 (CCH$_3$); 149.6, 154.7 (CO carbamates); 172.4 (CO lactam); 206.7 (CO ketone). HPLC: tr=12.454 min. LC/MS: tr=4.22 min: 371 [M+H$^+$]; 315 [(M+H$^+$)-tBu]; 271 [(M+H$^+$)-Boc]; 259 [(M+H+)-2 tBu]; 215, [(M+H+)-Boc-tBu]; 171 [(M+H+)-2 Boc]. HR-MS: 371.2167 Th (calculated=371.2182 Th) for C18H30N2O6.

The compounds (I-g) and (I-h) were synthesized from compound (III-f) following the same procedure and the same preparation, respectively using as alkylating agents benzyl bromide and allyl bromide.

(3R,5R)1-tert-butoxycarbonyl-3-tert-butoxycarbonylamino-5-isopropyl-3-benzylpyrrolidine-2,4-dione (I-g)

Yield: 42%. Colourless crystals. Melting point: 114° C. (not corrected)

[α]D20=+20 (c=2.01 dichloromethane). Circular dichroism: trifluoroethanol (λnm,θ): 193, 47500; 205.0; 225, .

−18000; 250, −11000. $^1$H-NMR (CDCl$_3$, 200 MHz): δ 1.01 (d, 3H, CH$_3$CH, J=6.8 Hz); 1.08 (d, 3H, CH$_3$CH, J=7.0 Hz); 1.32 (s, 9H, CH$_3$C); 1.56 (s, 9H, CH$_3$C); 1.92-2.16 (m, 1H, CHCH$_3$); 3.03 (sb, 2H, CH$_2$); 4.47 (d, 1H, CH*, J=5.6 Hz); 5.11 (sb, 1H, NH); 7.15-7.40 (m, 5H, Harom). $^{13}$C-NMR (CDCl$_3$, 100 MHz): δ 18.7, 19.3 (CH$_3$CH); 28.0 (CH$_3$C); 30.1 (CH); 38.0 (CH$_2$); 61.8 (CCH$_2$Ph); 69.7 (CH*); 81.4, 84.0 (CCH3); 128.2-131.8 (Carom); 149.8, 154.8 (CO carbamate); 171.7 (CO lactam); 206.1 (CO ketone). HPLC tr=14.324 min; LC/MS: tr=4.83 min: 447[M+H$^+$]; 391 [(M+H$^+$)-tBu]; 347 [(M+H$^+$)-Boc]; 291 [(M+H$^+$)-Boc-tBu]. HR-MS 447.2521 Th (calculated=447.2495 Th) C24H34N2O6.

(3R,5R)1-tert butoxycarbonyl-3-tert-butoxycarbonylamino-5-isopropyl-3-allylpyrrolidine-2,4-dione (I-h)

Yield: 42%. Colourless crystals. Melting point: 83° C. (not corrected). [α]D20=+15 (c=1.92, dichloromethane). Circular dichroism: trifluoroethanol (λnm,θ): 193, 33 000; 206, 0; 225, −11000; 250, −13000. $^1$H-NMR (CDCl$_3$, 200 MHz): δ 0.98 (d, 3H, CH$_3$CH, J=7.0 Hz); 1.22 (d, 3H, CH$_3$CH, J=7.1 Hz); 1.38 (s, 9H, CH$_3$C); 1.58 (s, 9H, CH$_3$C); 2.34-2.61 (m, 3H, CHCH$_3$ and CH$_2$CH=CH$_2$); 4.52 (d, 1H, CH*, J=4.4 Hz); 5.21-5.37 (m, 3H, NH and CH$_2$=CH); 5.82-6.03 (m, 1H, CH=CH$_2$).

Example 6

Synthesis of (R) 4-allyloxy-3-tert-butoxycarbonylamino-5-isopropyl-1-tert-butoxycarbonyl-1,5-dihydropyrrol-2-one (VIII-i) and of (3S,5R)-3-allyl-3-tert-butoxycarbonylamino-5-isopropyl-1-tert-butoxycarbonylpyrrolidine-2,4-dione (IX-i)

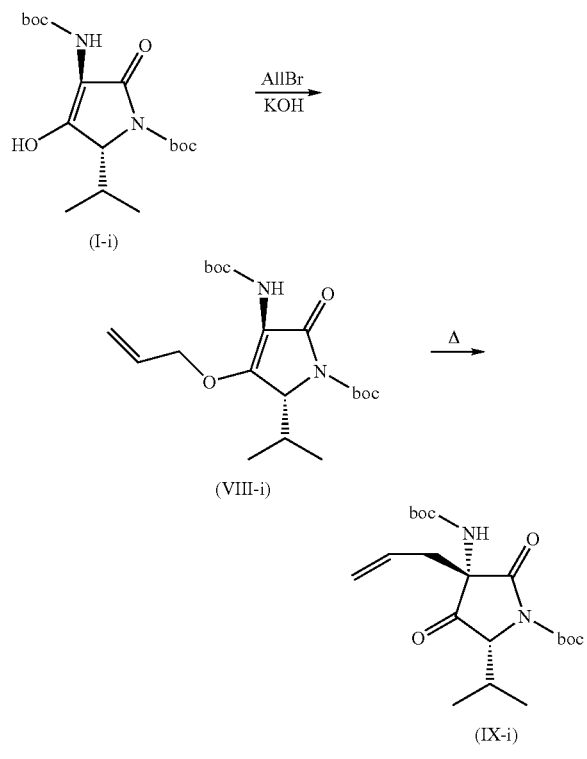

(R) 4-allyloxy-3-tert-butoxycarbonylamino-5-isopropyl-1-tert-butoxycarbonyl-1,5-dihydropyrrol-2-one (VIII-i)

To a solution of compound (I-i) (0.521 g, 1.46 mmol) in dehydrated DMSO (5.5 mL), powder KOH was added (0.074 g, 1.32 mmol) under stirring. Slight heating proved to be necessary for complete dissolution. The mixture coloured, changing from pink to dark purple. Allyl bromide (0.11 mL, 1.32 mmol) was then added and the reaction mixture was stirred 6 hours under an argon atmosphere. AcOEt (11 mL) was then added. The organic phase was washed with 0.1N HCl, dried over anhydrous magnesium sulphate and concentrated in vacuo. The crude residue was purified by chromatography on silica gel column (dichloromethane/AcOEt 100:0→80:20) which gave the allyloxy derivative (VIII-i) (0.365 g) in the form of a white powder with a yield of 60%.

[α]D20=−23 (c=0.24, MeOH). $^1$H-NMR (CDCl$_3$, 200 MHz): δ 0.90 (d, 3H, CH$_3$CH, J=7.0 Hz); 1.14 (d, 3H, CH$_3$CH, J=7.2 Hz); 1.48 (s, 9H, CH$_3$C); 1.56 (s, 9H, CH$_3$C); 2.45-2.53 (m, 1H, CHCH$_3$); 4.20 (d, 1H, CH*, J=3.2 Hz); 4.90 (m, 2H, CH$_2$O): 5.29 (d, 2H, CH$_2$=CH, J=1.4 Hz); 5.65 (sb, 1H, NH); 5.93-6.02 (m, 1H, CH=CH$_2$). $^{13}$C-NMR (CDCl$_3$, 100 MHz): δ 15.9, 18.6 (CH$_3$CH); 28.1 (CH$_3$C); 29.8 (CH CH$_3$); 62.6 (CH*); 71.3 (CH$_2$O); 81.1, 82.8 (CCH$_3$); 104.7 (CvinN); 118.9 (CH$_2$=CH); 132.1 (CH=CH$_2$); 149.2, 155.2 (CO carbamates); 165.5, 167.6 (CvinO and Co lactam). HPLC; tr=13.220 min, LC/MS: tr=3.06 min: [M+Na$^+$]=419; [M+H$^+$]=397; [(M+H$^+$)-tBu]=341; [(M+H$^+$)-2 tBu]=285; ((M+H$^+$)-Boc-tBu]=241. HR-MS: 397.2326 Th (calculated=397.2339 Th).

(3S,5R)-3-allyl-3-tert-butoxycarbonylamino-5-isopropyl-1-tert-butoxycarbonylpyrrolidine-2,4-dione (IX-i)

A solution of compound (VIII-i) (0.180 g, 0.45 mmol) in trifluorotoluene (3 mL) was irradiated for 30 min at 170° C. (Biotage device). The medium was then concentrated in vacuo and the crude residue was purified by chromatography on silica gel column (dichloromethane-AcOEt) which, after concentration of the solvent, gave compound (IX-i) in the form of white crystals (0.088 g, 50% yield).

[α]D20=−88 (c: 1.34 dichloromethane). $^1$H-NMR (CDCl$_3$, 200 MHz): δ 1.13 (d, 3H, CH$_3$CH, J=7.2 Hz); 1.17 (d, 3H, CH$_3$CH, J=7.5 Hz); 1.39 (s, 9H, CH$_3$C); 1.58 (s, 9H, CH$_3$C); 2.47 (d, 2H, CH$_2$CH=CH$_2$, J=7.5 Hz); 2.48 to 2.59 (m, 1H, CHCH$_3$); 4.21 (d, 1H, CH*, J=4.9 Hz); 5.04 (sb, 1H, NH); 5.23-5.33 (m, 2H, CH$_2$=CH); 5.59-5.80 (m, 1H, CH=CH$_2$). $^{13}$C-NMR (CDCl$_3$, 100 MHz): δ 19.0 and 19.2 (CH$_3$CH); 28.0 and 28.1 (CH$_3$C); 31.0 (CH CH$_3$); 39.2 (CH$_2$CH=CH$_2$); 63.6 (Cquat); 68.1 (CH*); 81.1, 84.0 (C CH$_3$); 122.6 (CH$_2$=CH); 128.3 (CH=CH$_2$); 149.8, 153.9 (CO carbamates); 170.5 (CO lactam); 205.9 (CO ketone). HPLC: tr=13.411 min; LC/MS: tr=4.62 min: 397 [M+H$^+$]; 341 [(M+H$^+$)-tBu]; 297 [(M+H$^+$)-Boc]; 285 [(M+H$^+$)-2tBu]; 197 [(M+H$^+$)-2 Boc]. HR-MS: 397.2318 Th (calculated=397.2339 Th) for C20H32N2O6.

Example 7

Synthesis of the Spiro Derivative D-Val-Baikiain (XI-a)

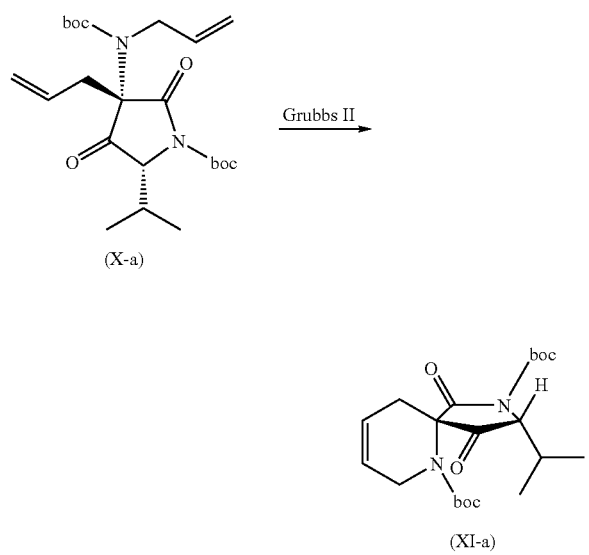

To a solution of diallylpyrrolidinedione (X-a) (0.105 g, 0.24 mmol) in refluxed dichloromethane (5 mL), Grubbs catalyst was added (benzylidene-[1,3-bis-(2,4,6-trimethylphenyl)-2-imidazolidinylidene]-dichloro(tricyclohexylphosphane) ruthenium (0.004 g, 0.0048 mmol, 2% mol) in 2 mL of the same solvent, under stirring. After 2 hours, the reaction medium was deactivated with DMSO (0.02 mL, 0.24 mml, 50 equiv relative to the catalyst), then the mixture was stirred for 12 hours and concentrated in vacuo. The crude mixture was purified by chromatography on silica gel column using dichloromethane as eluent. The compound (XI-a) (0.047 g, 48% yield) was isolated in the form of crystals after removal of the solvent by concentration in vacuo.

Melting point=124° C. (not corrected). [α]D20=−89 (c=1.90, CH$_2$Cl$_2$). $^1$H-NMR (CDCl$_3$, 300 MHz): δ 1.04 (d, 3H, CH$_3$CH, J=7.0 Hz); 1.08 (d, 3H, CH$_3$CH, J=7.2 Hz); 1.35 (s, 9H, CH$_3$C); 1.50 (s, 9H, CH$_3$C); 2.24-2.36 (m, 1H, CH$_2$Cquat); 2.40-2.52 (m, 2H, CHCH$_3$ and CH$_2$Cquat); 3.98-4.02 (m, 2H, CH$_2$N); 4.23 (d, 1H, CH*, J=4.5 Hz); 5.60-5.70 (m, 1H, CH=CHCH$_2$C); 5.86-5.94 (m, 1H, CH=CHCH$_2$N). $^{13}$C-NMR (CDCl$_3$, 75 MHz): δ 19.1, 19.2 (CH$_3$CH); 28.0, 28.2 (CH$_3$C); 30.6 (CH$_2$Cquat); 30.9 (CHCH$_3$); 43.6 (CH$_2$N); 62.8 (Cquat); 67.0 (CH*); 81.7, 83.8 (CCH$_3$); 118.5 (CCH$_2$CH=CH); 126.0 (NCH$_2$CH=CH); 150.0, 155.1 (CO carbamate); 171.1 (CO lactam); 206.2 (CO ketone). HPLC tr=14.275 min; LC/MS: tr=3.23 min; 409 [M+H$^+$]; 353 [(M+H$^+$)-tBu]; 297 [(M+H$^+$)-2 tBu]; 209 [(M+H$^+$)-2 Boc], HR-MS 409.2347 Th (calculated 409.2339 Th) for C21H32N2O6.

Example 8

Synthesis of (3R,5R)1-tert-butoxycarbonyl-3-tert-butoxycarbonylamino-3-(ethoxycarbonylmethyl)-5-isopropyl-pyrrolidine-2,4-dione (I-j) and (3aR,6R,6aS) 3a-(tert-butoxycarbonyl)-6-isopropyl-2,4-dioxohexahydrofuro[2,3-c]pyrrole-5-carboxylate of tert-butyl (XII-j)

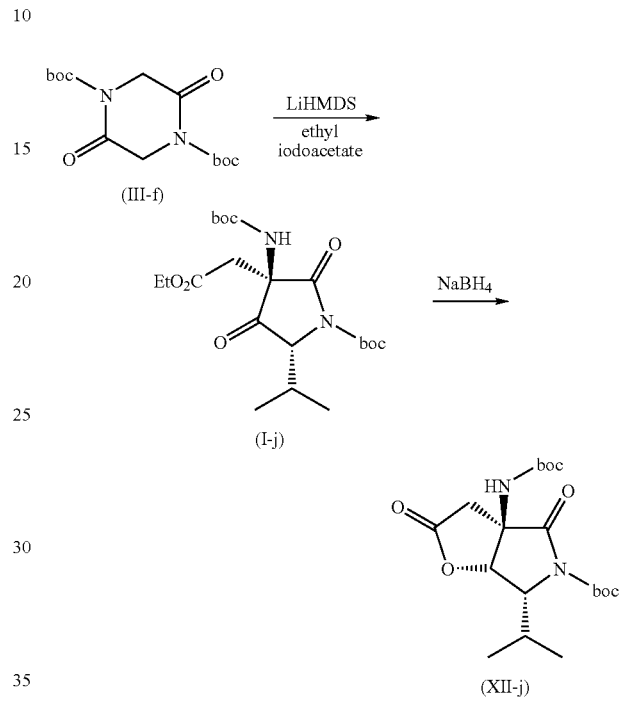

(III-f) was synthesized from 3 and from ethyliodoacetate in the presence of LiHMDS following the above-described procedure.

(3R,5R)1-tert-butoxycarbonyl-3-tert-butoxycarbonylamino-3-(ethoxycarbonylmethyl)-5-isopropyl pyrrolidine-2,4-dione (I-j)

Yellow oil; yield 49%. [α]D20=+21 (C=1.31, CH$_2$Cl$_2$). Rf=0.60 (hexane:AcOEt) (70:30). $^1$H-NMR (CDCl$_3$, 300 MHz): δ 0.98 (d, 3H, CH$_3$CH, J=7.0 Hz); 1.20 (d, 3H, CH$_3$CH, J=7.1 Hz); 1.29 (t, 3H, CH$_3$, CH$_2$, J=7.0 Hz); 1.37 (s, 9H, CH$_3$C); 1.56 (s, 9H, CH$_3$C); 2.36-2.49 (m, 1H, CHCH$_3$); 2.49-2.62 (m, 2H, CH$_2$Cquat); 4.05-4.28 (m, 2H, CH$_2$CH$_3$); 4.54 (d, 1H, CH*, J=4.3 Hz); 6.61 (sl, 1H, NH). $^{13}$C-NMR (CDCl$_3$, 75 MHz): δ 14.0 (CH$_3$CH$_2$); 17.7, 19.1 (CH$_3$CH); 27.9, 28.1 (CH$_3$C); 30.1 (CH); 34.8 (CH$_2$Cquat); 59.8 (Cquat); 69.9 (CH*); 81.4, 84.3 (CCH$_3$); 149.5, 155.0 (CO carbamates); 168.4 and 170.0 (CO lactam and CO ester); 204.6 (CO ketone). LC/MS: tr=4.73 min: [M+H$^+$]=443; [(M+H$^+$)-tBu]=387; ((M+H$^+$)-Boc]=343; [(M+H$^+$)-Boc-tBu]=287; [(M+H$^+$)-2 Boc]=243. HR-MS=443.2411 Th (calculated 443.2393 Th) for C21H34N2O8.

(3aR,6R,6aS) 3a-(tert-butoxycarbonyl)-6-isopropyl-2,4-dioxohexahydrofuro[2,3-c]pyrrole-5-carboxylate of tert-butyl (XII-j)

To a solution of (I-j) (0.040 g, 0.09 mmol) in a THF/water mixture (4:1), NaBH$_4$ (0.010 g, 0.27 mmol) was added at 0°

C. under stirring. After 30 min, AcOEt (10 mL) was added. The organic phase was washed with 0.1N HCl, dried over $MgSO_4$ and concentrated in vacuo. The crude residue was then purified by chromatography on silica gel column (dichloromethane:AcOEt 100:0→95:5). The compound (XII-j) was obtained with a yield of 75% (0.027 g) in the form of a colourless oil.

[α]D20=−23 (c=1.11 dichloromethane); Rf=0.61 (hexane: AcOEt (60:40). $^1$H-NMR (CDCl$_3$, 200 MHz): δ 0.91 (d, 3H, CH$_3$CH, J=7.0 Hz); 1.08 (d, 3H, CH$_3$CH, J=7.1 Hz); 1.37 (s, 9H, CH$_3$C); 1.48 (s, 9H, CH$_3$C); 2.42-2.58 (m, 1H, CHCH$_3$); 2.85 (d, 1H, CH$_2$, JAB=18.6 Hz); 2.94 (d, 1H, CH$_2$, JAB=18.6 Hz); 4.29 (t, 1H, CH*CH(CH$_3$)$_2$, J=6.3 Hz); 5.12 (sl, 1H, NHBoc); 5.20-5.26 (m, 1H, CH*O). $^{13}$C-NMR (CDCl$_3$, 100 MHz): δ 17.1, 17.9 (CH$_3$CH); 27.8, 28.2 (CH$_3$C); 29.7 (CHCH$_3$); 36.7 (CH$_2$); 63.1 (CH*CH(CH$_3$)$_2$); 63.6 (CCH$_2$CO); 80.6 (CH*O); 81.8 and 84.7 (CCH$_3$); 149.8, 154.5 (CO carbame); 171.6 and 172.0 (CO lactam and lactone). HPLC: tr=12.418 min; LC/MS: tr=4.34 min; [M+H$^+$]=399; [(M+H$^+$)-tBu]=343; [(M+H$^+$)-2 tBu]=287; [(M+H$^+$)-Boc-tBu]=243. HR-MS 399.2143 Th (calculated=399.2131 Th) for C19H30N2O7.

Example 9

Synthesis of (S)1-tert-butoxycarbonyl-3-(tert-butoxycarbonylamino)-3-isopropyl-3,4-dihydroquinoline-1(2H)-2,4-dione (I-k)

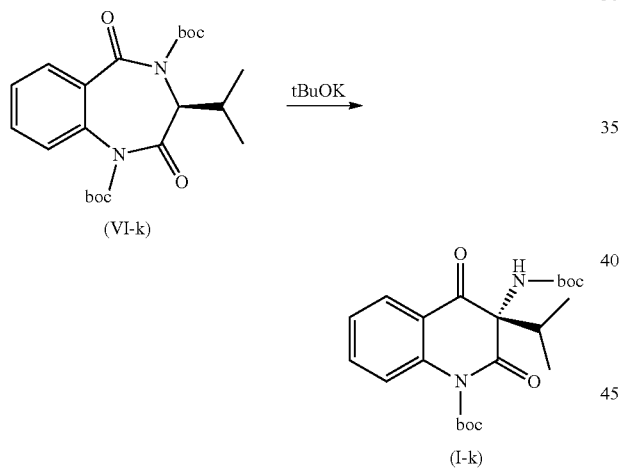

The compound (I-k) was obtained in the form of a colourless oil. Yield: 40% (non-optimized). [α]D20=+17 (c=0.87, CH$_2$Cl$_2$). $^1$H-NMR (CDCl$_3$, 300 MHz): δ 0.91 (d, 3H, CH$_3$CH, J=6.9 Hz; 0.95 (d, 3H, CH$_3$CH, J=6.9 Hz); 1.11 (s, 3H, CH$_3$C); 1.34 (s, 6H, CH$_3$C); 1.56, 1.59 (s, 9H, CH$_3$C); 2.12-2.24 (m, 1H, CHCH$_3$); 5.17 (s, 0.7H, NH); 5.21 (s, 0.3H, NH); 6.87-7.99 (m, 4H, Harom). $^{13}$C-NMR (CDCl$_3$, 75 MHz); δ 16.9, 17.0 (CH$_3$CH); 27.5, 28.2 (CH$_3$C); 35.3, 36.0 (CH); 71.9, 72.1 (Cquat); 80.9, 82.0, 86.1 86.6 (CCH$_3$); 114.7, 115.0, 123.9, 124.0, 135.7, 135.8 (CHarom); 120.2, 138.9 (Carom); 150.4, 153.8, 155.3 (CO carbamates); 169.5 (CO lactam); 191.6, 192.3 (CO ketone). The duplication of the isopropyl signals (proton) and aromatic/carbonyl groups (13C) was related to E/Z isomerism on the Boc lactam group. HPLC tr=13.178 min. LC/MS: tr=3.03 min: 419 [M+H$^+$]; 363 [(M+H$^+$)-tBu]; 319 ([(M+H$^+$)-Boc]; 263 [(M+H$^+$)-Boc-tBu]. HR-MS: 419.2173 Th (calculated 419.2182 Th) for C22H30N2O6.

The invention claimed is:

1. A method to synthesize a compound of following formula (I):

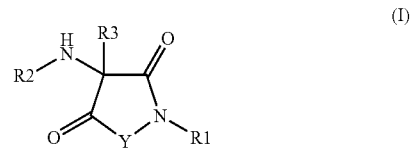

in which:

R1 and R2 are each independently a tert-butyloxycarbonyl (boc) group;

R3 is a hydrogen atom, a $C_1$ to $C_6$ alkyl group, a $C_1$ to $C_6$ arylalkyl group, a $C_2$ to $C_6$ alkenyl group or an alkoxycarbonylalkyl group;

Y is a —C(HR4)- group in which R4 is the hydrogen atom, a $C_1$ to $C_6$ alkyl group, an aryl group, a $C_1$ to $C_6$ arylalkyl group or a $C_2$ to $C_6$ alkenyl group; or an ortho-phenylene group, wherein it comprises:

a step (a$_1$) consisting of causing to react with a base chosen from the group consisting of potassium tert-butylate, sodium hydride, lithium diisopropylamine, lithium hexamethyldisilazane, potassium hexamethyldisilazane and dimethylaminopyridine, the compound of following formula (II):

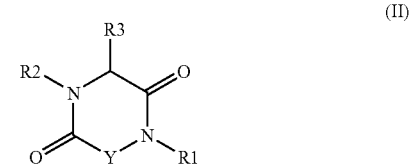

in which R1, R2, R3 and Y are as previously defined, or a step (a$_2$) consisting of causing to react with a base chosen from the group consisting of potassium tert-butylate, sodium hydride, lithium diisopropylamine, lithium hexamethyldisilazane, potassium hexamethyldisilazane and dimethylaminopyridine, the compound of following formula (III):

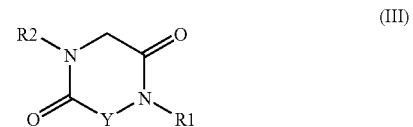

in the presence of a compound R3-X in which R1 and R2 are as defined previously, R3 is such as defined previously with the exclusion of hydrogen, and X is a halogen, or:

if Y is a —C(HR4)- group, a step (a$_3$) consisting of causing the compound of following formula (IV) to react with a base chosen from the group consisting of potassium tert-butylate, sodium hydride, lithium diisopropylamine, lithium hexamethyldisilazane, potassium hexamethyldisilazane and dimethylaminopyridine:

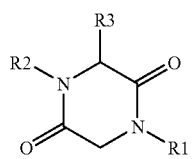

(IV)

in the presence of a compound of formula R4-X in which R1, R2, R3 are as previously defined, R4 is as previously defined with the exclusion of hydrogen, and X is a halogen, or:

if Y is a —C(HR4)- group, a step (a₄) consisting of causing to react with a base chosen from the group consisting of potassium tert-butylate, sodium hydride, lithium diisopropylamine, lithium hexamethyldisilazane, potassium hexamethyldisilazane and dimethylaminopyridine, the compound of following formula (V):

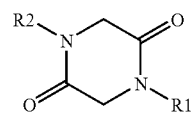

(V)

in the presence of a compound of formula R4-X, in which R1 and R2 are as previously defined, R3 is identical to R4 and is as defined previously with the exclusion of hydrogen, and X is a halogen.

2. The method according to claim 1, wherein, if Y is the ortho-phenylene group, step (a₁) consists of causing to react with a base the following compound of formula (VI):

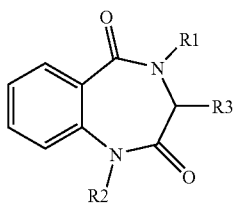

(VI)

in which R1, R2 and R3 are such as defined in claim 1.

3. The method according to claim 1, wherein R3 and R4 are each chosen independently from the group comprising isopropyl, benzyl, methyl, sec-butyl, prenyl, allyl, —CH₂COOC₂H₅ and —CH₂CH₂COOCH₃.

4. The method according to claim 1, wherein, if Y is a —C(HR4)- group and R3 and R4 are identical and are an allyl group, it comprises an additional step (b₁) consisting of submitting the compound of formula (I) to an intramolecular metathesis reaction of the olefins to give the following compound of formula (VII):

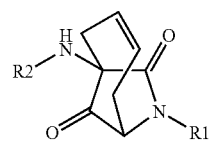

(VII)

in which R1 and R2 are as defined in claim 1.

5. The method according to claim 1, wherein if Y is the —C(HR4)- group, it comprises the following additional successive steps consisting of:

(b₂) causing the compound of formula (I) to react in a basic medium with an allyl halide to give the following compound (VIII):

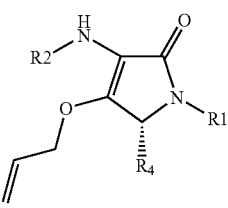

(VIII)

in which R1, R2 and R4 are such as defined in claim 1, (c) converting by heating the compound of formula (VIII) into the following compound of formula (IX):

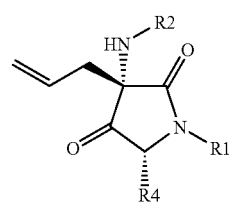

(IX)

in which R1, R2 and R4 are such as defined in claim 1, (d) causing the compound of formula (IX) to react with an allyl halide to form the following compound of formula (X):

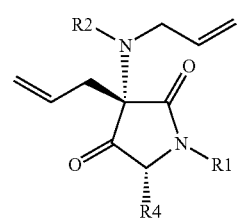

(X)

in which R1, R2 and R4 are such as defined in claim 1, and (e) converting the compound of formula (X,) by intramolecular metathesis of the olefins, into the following compound of formula (XI):

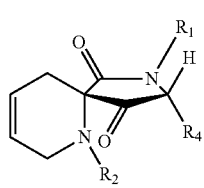

(XI)

in which R1, R2 and R4 are such as defined in claim 1.

6. The method according to claim 1 wherein, if R3 is the EtOOCCH₂ group and Y is the —C(HR4)- group, it comprises an additional step (b₃) consisting of causing the compound of formula (I) to react with a borohydride, to form the following compound of formula (XII):

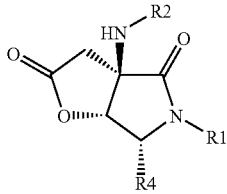

(XII)

in which R1, R2 and R4 are such as defined in claim 1.

7. The method according to claim 1 wherein, if Y is a —(CHR4)- group, it comprises an additional step ($b_4$) consisting of causing the compound of formula (I) to react with trifluoroacetic acid at a weight concentration of between 3% and 10%, to give the following compound of formula (XIII):

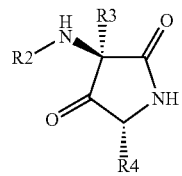

(XIII)

in which R2, R3 and R4 are such as defined in claim 1.

8. The method according to claim 7, wherein it comprises an additional step ($c_4$) consisting of causing the compound of formula (XIII) to react with a borohydride to form the following compound of formula (XIV):

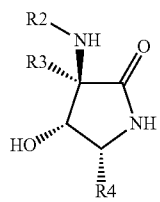

(XIV)

in which R2, R3 and R4 are such as defined in claim 1.

9. The method according to claim 7, wherein it comprises an additional step ($c_5$) consisting of causing the compound of formula (XIII) to react with trifluoroacetic acid at a weight concentration of between 10% and 25%, to give the following compound of formula (XV):

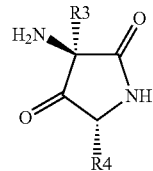

(XV)

in which R3 and R4 are such as defined in claim 1.

10. A compound of the following formula (XVII):

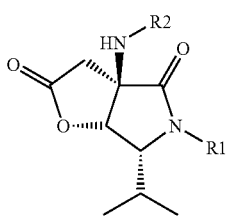

(XVII)

and its pharmaceutically acceptable salts, in which R1 and R2 are each independently a tert-butyloxycarbonyl (boc) group.

11. A compound of the following formula (XVIII):

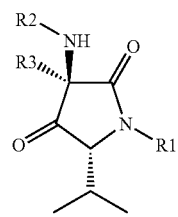

(XVIII)

and its pharmaceutically acceptable salts, in which:
R1 and R2 each independently are a tert-butyloxycarbonyl (boc) group;
R3 is a methyl, benzyl, allyl, prenyl group or —$CH_2COOC_2H_5$.

12. A method according to claim 5, wherein R4 is isopropyl.

13. A method according to claim 6, wherein the borohydride is $NaBH_4$.

14. The method according to claim 5, wherein converting by heating the compound of formula (VIII) into the compound of formula (IX) in step (c) is performed by heating in a microwave.

15. A method according to claim 8, wherein the borohydride is $NaBH_4$.

* * * * *